US008869666B2

(12) United States Patent
Yang et al.

(10) Patent No.: US 8,869,666 B2
(45) Date of Patent: Oct. 28, 2014

(54) MICROTOME WITH SURFACE ORIENTATION SENSOR TO SENSE ORIENTATION OF SURFACE OF SAMPLE

(75) Inventors: Hwai-Jyh Michael Yang, Cerritos, CA (US); Xuan S. Bui, Torrance, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 469 days.

(21) Appl. No.: 13/071,185

(22) Filed: Mar. 24, 2011

(65) Prior Publication Data

US 2012/0240737 A1    Sep. 27, 2012

(51) Int. Cl.
*B26D 5/00* (2006.01)
*G01N 1/00* (2006.01)
*G01N 1/06* (2006.01)

(52) U.S. Cl.
CPC .............. *G01N 1/06* (2013.01); *Y10S 83/9155* (2013.01)
USPC .................. 83/360; 83/367; 83/368; 83/915.5

(58) Field of Classification Search
USPC ........... 83/915.5, 421, 36, 733, 367, 360, 368
See application file for complete search history.

(56) References Cited

U.S. PATENT DOCUMENTS

| 2,155,523 | A | | 4/1939 | Bausch et al. |
| 3,926,085 | A | | 12/1975 | Shatzel |
| 5,065,657 | A | * | 11/1991 | Pfeifer ............................ 83/703 |
| 5,099,735 | A | | 3/1992 | Kempe et al. |
| D326,860 | S | | 6/1992 | Holbl |
| D326,921 | S | | 6/1992 | Holbl |
| D328,129 | S | | 7/1992 | Holbl |
| 5,156,019 | A | | 10/1992 | McCormick |
| 5,161,446 | A | | 11/1992 | Holbl et al. |
| 5,226,335 | A | * | 7/1993 | Sitte et al. ........................ 83/74 |
| 5,255,585 | A | | 10/1993 | Gordon |
| 5,299,481 | A | | 4/1994 | Lihl et al. |
| D358,895 | S | | 5/1995 | Holbl |
| 5,535,654 | A | * | 7/1996 | Niesporek et al. .............. 83/364 |
| 5,609,083 | A | * | 3/1997 | Persson ............................ 83/14 |
| D383,548 | S | | 9/1997 | Hoelbl |
| 5,669,278 | A | | 9/1997 | Metzner |

(Continued)

FOREIGN PATENT DOCUMENTS

| EP | 2503315 | 9/2012 |
| WO | WO-9115746 | 10/1991 |
| WO | WO-2010081497 | 7/2010 |

OTHER PUBLICATIONS

Sakura Finetek U.S.A., Inc., et al., European search report dated Dec. 3, 2012 for EP Appln. No. 12159609.2.

(Continued)

*Primary Examiner* — Omar Flores Sanchez
(74) *Attorney, Agent, or Firm* — Blakely Sokoloff Taylor & Zafman LLP

(57) ABSTRACT

A sample sectioning device includes a cutting mechanism, a sample holder, a drive system, and a surface orientation sensor. The sample holder is operable to hold a sample. The cutting mechanism is operable to cut sections from the sample. The drive system is coupled with the sample holder. The drive system is operable to drive movement between the sample held by the sample holder and the cutting mechanism. The surface orientation sensor is operable to sense an orientation of a surface of the sample held by the sample holder.

21 Claims, 9 Drawing Sheets

(56) References Cited

U.S. PATENT DOCUMENTS

| | | | |
|---|---|---|---|
| 5,673,905 A | 10/1997 | Kiene | |
| 5,695,942 A | 12/1997 | Farmilo et al. | |
| 5,711,200 A | 1/1998 | Thiem | |
| 5,740,708 A | 4/1998 | Tabone | |
| 5,782,572 A | 7/1998 | Thiem | |
| 5,817,032 A | 10/1998 | Williamson, IV et al. | |
| 5,881,626 A | 3/1999 | Kiene et al. | |
| 5,964,138 A | 10/1999 | Metzner et al. | |
| 5,965,454 A | 10/1999 | Farmilo et al. | |
| 5,974,811 A | 11/1999 | Heid et al. | |
| 6,041,686 A | 3/2000 | Lihl et al. | |
| 6,058,788 A | 5/2000 | Thiem et al. | |
| 6,058,824 A | 5/2000 | Neymeyr | |
| 6,080,365 A | 6/2000 | Thiem et al. | |
| 6,178,757 B1 | 1/2001 | Sitte et al. | |
| 6,231,037 B1 | 5/2001 | Metzner | |
| 6,253,653 B1 | 7/2001 | Walter et al. | |
| 6,349,264 B1 | 2/2002 | Rhett et al. | |
| 6,387,653 B1 | 5/2002 | Voneiff et al. | |
| 6,568,307 B1 | 5/2003 | Gunther et al. | |
| 6,598,507 B1 | 7/2003 | Gunther et al. | |
| 6,634,268 B1 | 10/2003 | Guenther et al. | |
| 6,635,225 B1 | 10/2003 | Thiem et al. | |
| 6,644,162 B1 | 11/2003 | Temple et al. | |
| 6,705,187 B2 | 3/2004 | Konrad | |
| 6,715,870 B2 | 4/2004 | Kiene et al. | |
| 6,763,972 B2 | 7/2004 | Graupner | |
| 6,766,593 B2 | 7/2004 | Laudat et al. | |
| 6,827,900 B2 | 12/2004 | Thiem et al. | |
| 6,860,113 B2 | 3/2005 | Goll | |
| 7,044,038 B2 | 5/2006 | Hess | |
| 7,080,583 B2 | 7/2006 | Lihl et al. | |
| 7,104,666 B2 | 9/2006 | Lihl et al. | |
| 7,111,535 B2 | 9/2006 | Hess | |
| 7,168,694 B2 | 1/2007 | Bui et al. | |
| 7,168,901 B2 | 1/2007 | Ranner | |
| 7,240,497 B2 | 7/2007 | Dorenkamp et al. | |
| 7,273,000 B2 | 9/2007 | Thiem et al. | |
| 7,287,388 B2 | 10/2007 | Dorenkamp et al. | |
| 7,313,993 B2 | 1/2008 | Foerderer | |
| 7,357,384 B2 | 4/2008 | Thiem | |
| 7,371,346 B2 | 5/2008 | Windeyer et al. | |
| 7,374,907 B1 | 5/2008 | Voneiff et al. | |
| 7,600,457 B2 | 10/2009 | Voneiff et al. | |
| 7,673,546 B2 | 3/2010 | Dorenkamp et al. | |
| 8,001,876 B1 | 8/2011 | Tabb et al. | |
| 8,056,456 B2 * | 11/2011 | Walter | 83/76.8 |
| 8,074,545 B1 | 12/2011 | Tabb et al. | |
| 8,256,332 B2 * | 9/2012 | Walter | 83/76.8 |
| 8,353,232 B2 * | 1/2013 | Walter et al. | 83/13 |
| 2003/0022271 A1 | 1/2003 | Voneiff et al. | |
| 2003/0101858 A1 * | 6/2003 | Tamura et al. | 83/575 |
| 2005/0235542 A1 | 10/2005 | Metzner et al. | |
| 2006/0179992 A1 | 8/2006 | Kermani | |
| 2007/0091428 A1 | 4/2007 | Wilson | |
| 2007/0180965 A1 | 8/2007 | Ito et al. | |
| 2007/0193990 A1 | 8/2007 | Richerzhagen | |
| 2008/0072722 A1 | 3/2008 | Tanki et al. | |
| 2008/0113440 A1 | 5/2008 | Gurney et al. | |
| 2009/0241751 A1 | 10/2009 | Walter | |
| 2010/0000390 A1 | 1/2010 | Fank | |
| 2010/0064867 A1 | 3/2010 | Schmitt | |

OTHER PUBLICATIONS

Sakura Finetek U.S.A., Inc., Examination Report dated Apr. 1, 2014, Australian Appln. No. 2012200721, 3 pages.
Sakura Finetek U.S.A., Inc., International Search Report and Written Opinion mailed Jun. 21, 2013 for PCT/US2012/068747, 19 pages.

* cited by examiner

MICROTOME WITH SURFACE ORIENTATION SENSOR TO SENSE ORIENTATION OF SURFACE OF SAMPLE

BACKGROUND

1. Field

Embodiments of the invention relate to microtomes or other tissue sample sectioning devices to produce sections of samples, specifically some embodiments relate to microtomes or other tissue sample sectioning devices that have surface orientation sensors to sense orientations of surfaces of the samples.

2. Background Information

Histology is a science or discipline associated with the processing of tissue for examination or analysis. The examination or analysis may be of the cellular morphology, chemical composition, tissue structure or composition, or other tissue characteristics.

In histology, a sample of tissue may be prepared for sectioning by a microtome or other sample sectioning device. Commonly, the tissue may be dried or dehydrated by removing most or almost all of the water from the tissue, for example by exposing the tissue to one or more dehydrating agents. After drying the tissue, clearing of the dehydrating agents may optionally be performed, and then an embedding agent (e.g., wax with added plasticizers) may be introduced or infiltrated into the dried tissue. The removal of the water and the infiltration of the embedding agent may aid in sectioning the tissue into thin sections with the microtome.

Embedding may then be performed on the tissue. During embedding, the tissue that has been dried and infiltrated with the embedding agent may be embedded in a block or other mass of wax, various polymers, or another embedding medium. Representatively, the dried and wax-infiltrated tissue may be placed in a mold and/or cassette, melted wax may be dispensed over the tissue until the mold has been filled with the wax, and then the wax may be cooled and hardened. Embedding the tissue in the block of wax may help to provide additional support during cutting or sectioning of the tissue with a microtome.

The microtome may be used to cut thin slices or sections of the sample of tissue. Various different types of microtomes are known in the arts. Representative types include, for example, sled, rotary, vibrating, saw, and laser microtomes. The microtomes may be manual or automated. Automated microtomes may include motorized systems or drive systems to drive or automate a cutting movement between the sample from which the sections are to be cut and a cutting mechanism used to cut the sections. It is to be appreciated that microtomes may also be used for other purposes besides just histology, and that microtomes may be used on other types of samples besides just embedded tissue.

BRIEF DESCRIPTION OF THE SEVERAL VIEWS OF THE DRAWINGS

The invention may best be understood by referring to the following description and accompanying drawings that are used to illustrate embodiments of the invention. In the drawings.

DETAILED DESCRIPTION

In the following description, numerous specific details, such as particular microtomes, particular cutting drive systems, particular sensors, particular sensing mechanisms, particular surface orientation measurement and/or adjustment processes, and the like, are set forth. However, it is understood that embodiments of the invention may be practiced without these specific details. In other instances, well-known mechanical components, circuits, structures and techniques have not been shown in detail in order not to obscure the understanding of this description.

Figure 1:
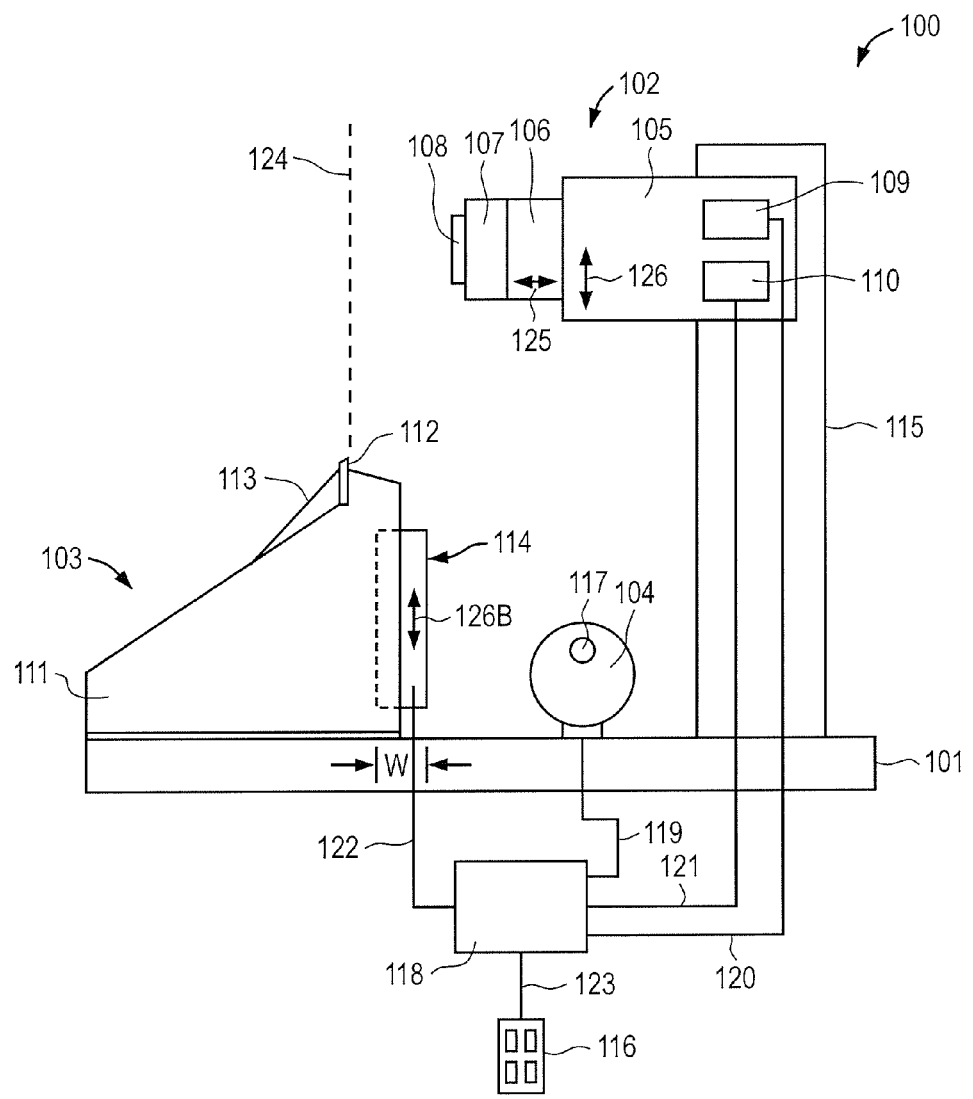
FIG. 1 illustrates a schematic view of an embodiment of a microtome or other sample sectioning device.

FIG. 1 illustrates a schematic view of an embodiment of a microtome or other sample sectioning device. Microtome 100 may include base member 101 having feed drive system or cutting drive system 102, mounting member 103 and handwheel 104 attached thereto. Feed drive system 102 may be supported above base member 101 by support member 115. Feed drive system 102 may include vertical drive member 105, horizontal drive member 106 and sample holder 107 operable to hold sample 108. Sample 108 may include a piece of tissue that is to be sectioned, for example, a piece of tissue embedded in paraffin. The cutting drive system or feed drive system is operable to drive movement of the sample held by the sample holder. Motor 109 of feed drive system 102 may be mechanically coupled to vertical drive member 105 and operable to drive vertical movement of vertical drive member 105 in a direction of vertical double arrow 126. Motor 110 of feed drive system 102 may be mechanically coupled to horizontal drive member 106 to drive horizontal movement of horizontal drive member 106 in a direction of horizontal double arrow 125. It should be noted that terms such as "horizontal", "vertical", "top", "bottom", "upper", "lower", and the like, are used herein to facilitate the description of the illustrated device. It is possible for other devices to replace horizontal movements with vertical movements, etc.

Mounting member 103 may include mounting base 111 which provides a mounting surface for cutting member or mechanism 112. Cutting member or mechanism 112 may be, for example, a blade or knife of various types of materials mounted to mounting member 103, or other types of cutting mechanisms suitable for microtomes. Section receiving member 113 may be positioned along one side of cutting member 112. Section receiving member 113 is dimensioned to receive a section cut from sample 108 by cutting member or blade 112. In this aspect, section receiving member 113 may have an inclined surface extending from a cutting edge of blade 112 to the surface of mounting member 103. As cutting member or blade 112 slices through sample 108, the section cut from sample 108 is separated from sample 108 and extends along section receiving member 113.

As shown, in some embodiments, microtome 100 may include a surface orientation sensor assembly 114. Surface orientation sensor assembly 114 is operable to sense or measure an orientation or angle of a surface of sample 108. The orientation or angle of the surface of sample 108 may be sensed or determined in various different ways. In some embodiments, which are described in further detail below, the surface of sample 108 may contact sensor assembly 114, and one or more movable portions of sensor assembly 114 may conform to an orientation of the surface of sample 108. The movement of the one or more movable portions of sensor assembly may allow microtome 100 to autonomously sense or determine the orientation of the surface of sample 108. Optical and other sensing mechanisms are also suitable.

The sensed orientation may be used to adjust or align the surface of the sample 108 so that it is parallel, substantially parallel, or at least more parallel with cutting member or mechanism 112 and/or cutting plane 124 associated with cutting member or mechanism 112. It is advantageous that the surface of sample 108 be sufficiently aligned parallel with cutting member 112 and/or cutting plane 124 so that the sample sections cut by microtome 100 are sufficiently evenly cut. In some embodiments, microtome 100 may optionally be capable of autonomously adjusting or aligning the orientation of surface of sample 108 parallel, sufficiently parallel, or at least more parallel, with cutting member 112 and/or cutting plane 124. Microtome 100 may have logic to autonomously sense and/or adjust an orientation of the surface of the sample relative to a cutting plane and/or cutting mechanism based on the sensed orientation. Advantageously, this may help to improve alignment accuracy and/or relieve an operator from performing the adjustment manually. Alternatively, the adjustment may be performed manually, if desired. An embodiment of a method of sectioning may include microtome 100 autonomously sensing an orientation of a surface of sample 108 using sensor assembly 114, an operator manually or microtome 100 autonomously adjusting the orientation of the surface of sample 108, and microtome 100 taking a section of sample 108 after such adjustment.

In the illustrated embodiment, sensor assembly 114 is movably coupled to mounting base 111 at a position between feed drive system 102 and mounting member 103, although this is not required. Mounting base 111 provides a support surface for sensor assembly 114 and is dimensioned and coupled to accommodate sliding of sensor assembly 114 vertically in a direction of vertical double arrow 126B. During operation, sensor assembly 114 is operable to slide along mounting base 111 in an upward vertical direction toward feed drive system 102, and vertical drive member 105 is operable to cause feed drive system 102 to move in a downward vertical direction toward sensor assembly 114. Once sample 108 is sufficiently vertically aligned with sensor assembly 114, horizontal drive member 106 is operable to cause feed drive system 102 to move in a horizontal direction toward sensor assembly 114 in the direction of horizontal arrow 125 so that a surface of sample 108 is appropriately positioned relative to sensor assembly 114 to allow for surface orientation measurement. Once the orientation of the surface of sample 108 is determined, and realigned if appropriate, sensor assembly 114 is operable to retract in a vertical downward direction as viewed (e.g., to a retracted position away from the movement between the sample held by the sample holder and the cutting mechanism.)

Referring again to FIG. 1, operation of feed drive system 102 may be controlled using handwheel 104 and/or control device 116. Handwheel 104 may include handle or other pulse generating device 117 to lock the handwheel 104. Rotation of handwheel 104 may be operable to cause vertical drive member 105 to move in a vertical direction shown by vertical double arrow 126 to facilitate slicing of sample 108. In some embodiments, handwheel 104 may be a decoupled handwheel, which is not mechanically coupled to feed drive system 102. Rather, decoupled handwheel 104 may be electrically connected to an encoder (not shown) and control circuit 118 via control line 119. The rotation of decoupled handwheel 104 may cause the encoder to deliver an electrical signal to control circuit 118. Control circuit 118 is connected to motor 109 via control line 120 and is operable to control movement of vertical drive member 105 according to the electrical signal from the encoder. Control circuit 118 is also connected to motor 110 via control line 121 and is connected to sensor assembly 114 via control line 122.

In addition to signals from the encoder, signals from control device 116 may be transmitted to control circuit 118 to control or facilitate operation of sensor assembly 114, handwheel 104, motor 109 and/or motor 110. In some embodiments, control device 116 may be, for example, a keyboard, a capacitive sensor touch pad, or other user or data input device. In some embodiments, signals are transmitted between control device 116 and control circuit 118 via control line 123. In other embodiments, control device 116 is a wireless control device that is operable to wirelessly transmit signals to control circuit 118 and control line 123 is omitted.

Figure 2:
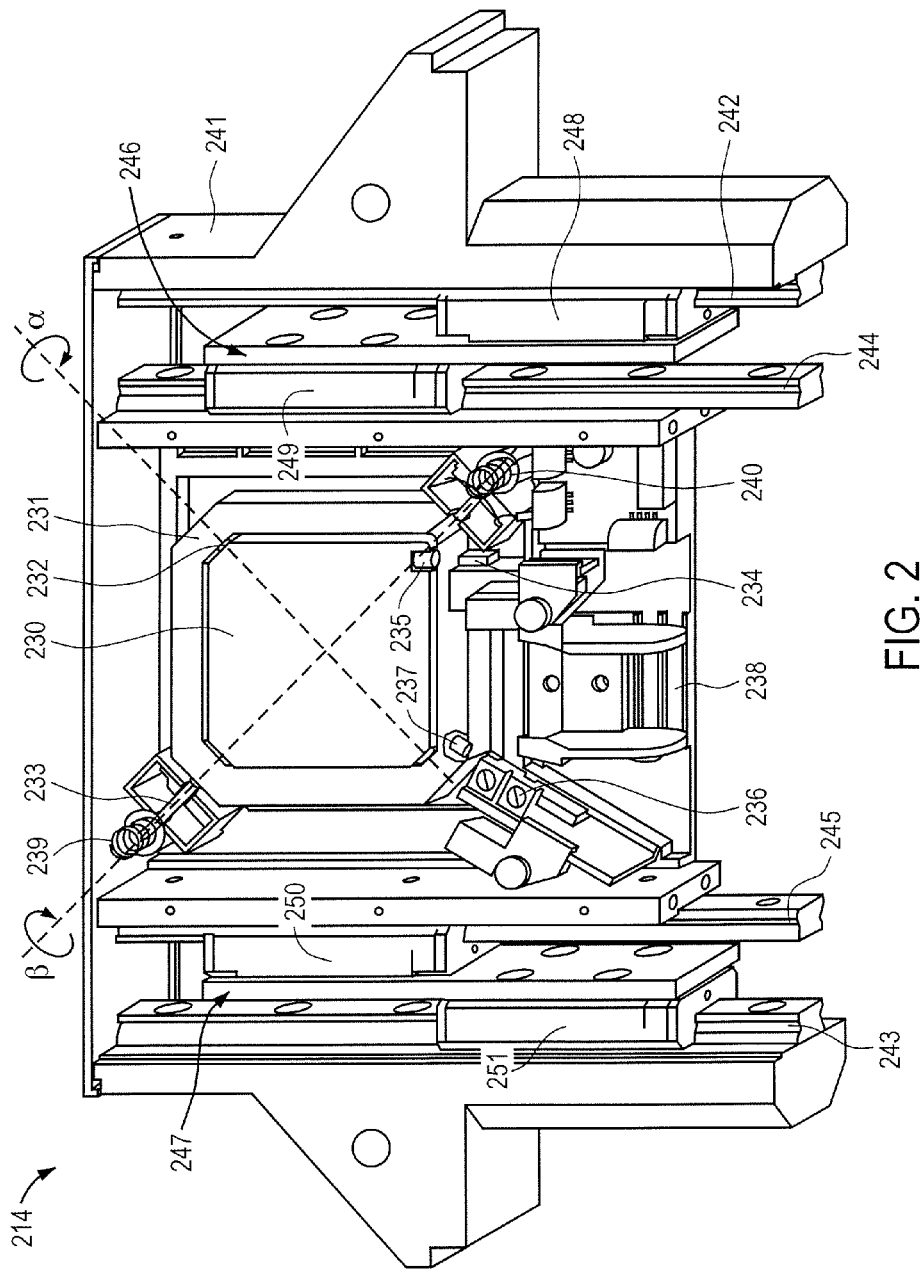
FIG. 2 illustrates an embodiment of a sensor assembly for a microtome or other sample sectioning device.

FIG. 2 illustrates an embodiment of a surface orientation sensor assembly. In the figures, where considered appropriate, reference numerals or terminal portions of reference numerals have been repeated among the figures to indicate corresponding or analogous elements, which may optionally have similar characteristics. For example, surface orientation sensor assembly 214 in FIG. 2 may optionally have similar characteristics to sensor assembly 114 in FIG. 1. Surface orientation sensor assembly 214 is used to facilitate autonomous alignment of a surface of a sample with a cutting mechanism and/or cutting plane. It is advantageous that the surface of the sample be sufficiently aligned parallel to the cutting mechanism (e.g., a blade) so that sections are cut evenly. To align the sample, the sample contacts sensor assembly 214 and sensor assembly 214 detects an orientation of the surface of the sample. In some cases, the surface of the sample will not be aligned parallel or sufficiently parallel with the cutting plane. Sensor assembly 214 detects the angle of the surface of the sample with respect to the cutting plane. Using the sensed information, the sample may be adjusted to an adjusted position where the surface of the sample is parallel, or at least more parallel, with the cutting plane.

The illustrated embodiment of the sensor assembly 214 includes sensing plate 230 and sensing frame 231. Sensing frame 231 is positioned around sensing plate 230. Sensing plate 230 may be planar and/or have a flat surface (e.g., be a planar plate). A thickness of sensing plate may be on the order of several millimeters (e.g., 0.5 mm to 5 mm) depending on the material. Dimensions across sensing plate may be on the order of about 20-60 mm. Sensing plate and sensing frame may be construted of various materials, such as, for example, aluminum, stainless steel, other metals, rigid plastics, and combinations thereof optionally coated with protective coatings. In the illustration, sensing plate 230 and sensing frame 231 are substantially square with respect to a length and a width dimension with the sensing plate having truncated corners and the sensing frame having conforming frame corner portions, but in alternate embodiments they may be more or less square, or may be rectangular, circular, oval, octagonal, hexagonal, or otherwise. In one particular example embodiment, the sensing plate is square with dimensions of approximately 39.5 mm×39.5 mm, is constructed of aluminum having a protective coating (e.g., a polytetrafluoroethylene (PTFE) coating), and the sensing frame is approximately 90 mm×75 mm×25 mm thick and made of metal (e.g., aluminum) and/or plastic. Alternatively, the sensing plate and sensing frame may have other dimensions and be made of other materials (e.g., stainless steel, other metals, or various types of plastic). Sensing plate 230 is a first sensing member that is rotatable about first axial support member 232, and sensing frame 231 is a second sensing member that is rotatable about second axial support member 233. First axial support member 232 diagonally bisects sensing plate 230. Second axial support member 233 diagonally bisects sensing frame 231. First axial support member 232 is substantially perpendicular to second axial support member 233 (for example 80-100 degrees). Accordingly, sensing plate 230 is rotatable along an axis orthogonal or perpendicular to the axis of rotation for sensing frame 231. Sensing plate 230 and sensing frame 231 are also movable in a horizontal direction when the sample is pressed against sensing plate 230. The movement in the horizontal direction may provide information about the horizontal position (i.e., into and out of the page as viewed) of the surface of sample. In this aspect, both an angular orientation of the surface of the sample, as well as a horizontal position of the surface of the sample with respect to the cutting plane can be detected by sensor assembly 214.

Sensor assembly 214 further includes sensing plate sensor 234 and sensing plate signal output member 235. Sensing plate sensor 234 is attached to sensing assembly frame 238 while sensing plate signal output member 235 is attached to sensing plate 230. As shown, in one aspect, sensing plate signal output member 235 may be attached to sensing plate 230 at or proximate a corner or other portion most distant from an axis of rotation of the sensing plate 230. Sensing plate sensor 234 is sufficiently aligned with sensing plate signal output member 235 to receive a signal from sensing plate signal output member 235. The signal received is indicative of an amount of rotation or displacement of sensing plate 230. By way of example, an angle of rotation ($\alpha$) of sensing plate 230 along first axial support member 232, typically on the order of several degrees (e.g., 0 to 10°) may be detected by sensing plate sensor 234 based on the degree of movement of sensing plate signal output member 235 and the corresponding strength of the signal received from sensing plate signal output member 235. In some embodiments, sensing plate signal output member 235 may include a magnet. In this embodiment, sensing plate sensor 234 is operable to sense a magnetic field of magnet 235 (for example through a magneto-resistive sensing mechanism) to detect a position of sensing plate 230. Alternatively, instead of using magnetism, other sensing mechanisms may be used, such as, for example, mechanical sensors (for example a strain gauge), electrical sensors (for example using capacitance), optical sensors, or other sensors may optionally be used.

Sensor assembly 214 also includes sensing frame sensor 236 and sensing frame signal output member 237. Sensing frame sensor 236 is attached to sensing assembly frame 238 while sensing frame signal output member 237 is attached to sensing frame 231. As shown, in one aspect, sensing frame signal output member 237 may be attached to sensing frame 231 at or proximate a corner or other portion most distant from the axis of rotation of the sensing frame 231. Sensing frame sensor 236 is sufficiently aligned with sensing frame signal output member 237 so that it can receive a signal from sensing frame signal output member 237. In one example, sensing frame signal output member 237 may include a magnet and sensing frame sensor 236 may detect a magnetic field or signal from sensing frame signal output member 237 to detect an angle of rotation ($\beta$) of sensing frame 231, which typically is on the order of several degrees (e.g., 0 to 10°). Alternatively, instead of using magnetism, other sensing mechanisms may be used. As previously discussed, second axial support member 233 of sensing frame 231 is substantially orthogonal to first axial support member 232 of sensing plate 230. Accordingly, the angle of the surface of the sample with respect to the cutting plane with respect to second axial support member 233 can further be detected by sensing frame sensor 236.

The angle of rotation ($\alpha$) of sensing plate 230 about first axial support member 232, and the angle of rotation ($\beta$) of sensing frame 231 about second axial support member 233, as detected by sensing plate sensor 234 and sensing frame sensor 236, respectively, in turn reflects a first orientation of the surface of the sample contacting sensor assembly 214. When sensing plate sensor 234 and sensing frame sensor 236 detect that the surface of the sample is not parallel or sufficiently parallel to the cutting plane, a signal may be provided from the sensor assembly 214 to a control component of microtome 100 (e.g., control circuit 118 and/or control device 116). The signal may represent the degree or extent that the cutting surface is offset from the cutting plane as determined from the rotation of sensing plate 230 and sensing frame 231. The control component may autonomously or under user direction cause the feed drive system to modify the orientation of the surface of the sample from an initial orientation to a changed orientation in which the cutting surface of the sample is more parallel with the cutting plane.

In one embodiment, calibration may be used to characterize a condition where sensing plate 230 and sensing frame 231 are aligned parallel with the cutting mechanism and/or the cutting plane. For example, sensing plate 230 and sensing frame 231 may be moved, for example manually or by being forced by a mechanical calibration piece, so that they are aligned parallel with the cutting mechanism and/or the cutting plane. Outputs of sensing plate sensor 234 and sensing frame sensor 236 may be determined as calibration data in this condition. For example, when sensing plate signal output member 235 and sensing frame signal output member 237 use a magneto-resistive sensing mechanism, the calibration data may include magneto-resistive values or indications of strengths of magnetic fields experienced by the respective sensing plate sensor 234 and sensing frame sensor 236. This calibration data may be stored in a machine-readable medium (e.g., a memory), or otherwise preserved by the microtome.

The calibration data may be accessed and used subsequently when adjusting the orientation of a surface of a sample. For example, the microtome may autonomously adjust a sample holder to adjust the orientation of the surface of the sample over a generally short period of time, while contact with the sensing plate and sensing frame is maintained. Throughout this process, multiple real-time sensor measurements may be made by each of sensing plate sensor 234 and sensing frame sensor 236. For example, in the case of a magneto-resistive sensing mechanism, multiple magneto-resistive measurements may be made in series after each adjustment of the sample holder. These real time measurements may be compared to the stored or preserved calibration data which correspond to the condition where sensing plate 230 and sensing frame 231 are aligned parallel with the cutting mechanism and/or cutting plane. As the orientation of the surface of the sample is adjusted to be more parallel with the cutting mechanism and/or the cutting plane, the real time measurements may become closer in value to the calibration values. Further adjustment may be performed until the current sensor output values (e.g., the magneto-resistive values) match or sufficiently match the calibration sensor values. When the current sensor output values match or sufficiently match the calibrated values, then it may be inferred that the surface of the sample is parallel or sufficiently parallel with the cutting mechanism and/or cutting plane.

Sensing plate 230 and sensing frame 231 are also movable in a horizontal direction (i.e., into and out of the page as viewed in this illustration). In this aspect, first biasing member 239 and second biasing member 240 may be positioned along ends of second axial support member 233 to bias second axial support member 233 in a direction toward the sample. In some embodiments, first biasing member 239 and second biasing member 240 may be springs. Pressing the surface of the sample against sensing plate 230 causes sensing frame 231 and second axial support member 233 to retract in the horizontal direction away from the sample. Optical or other sensors, which will be discussed in more detail in conjunction with the embodiment of FIG. 4C, may be positioned at or near each end of second axial support member 233, and may be operable to detect movement of second axial support member 233. For example, when second axial support member 233 breaks a light beam between a pair of optical sensors, further movement of the sample block may be terminated. In this aspect, a horizontal position of the foremost surface of the sample with respect to the cutting plane may be detected by sensor assembly 214. In addition to the measured position of the foremost surface of the sample (for example based on the measured horizontal displacement of second axial support member 233), the location of the cutting mechanism or cutting plane is also accurately known. Together, these pieces of information may be used to help the microtome make initial sections of accurate and known thickness.

As previously mentioned, in some embodiments sensing assembly frame 238 may be slideably or movably attached to mounting member 241, although this is not required, and in other embodiments, a sensor assembly 214 may have a fixed position below a cutting member or mechanism. Mounting member 241 may be fixedly attached to a mounting base (for example mounting base 111 of FIG. 1) used to support sensing assembly 214. Sensing assembly frame 238 may slide in a vertical direction along mounting member 241. In this aspect, mounting member 241 may include guide rails 242, 243, and sensing assembly frame 238 may include guide rails 244, 245. Sliding member 246 is slideably coupled to guide rails 242, 244, between mounting member 241 and sensing assembly frame 238 to allow sensing assembly frame 238 to slide with respect to mounting member 241. Sliding member 246 includes first guide member 248 and second guide member 249 extending from opposite sides of sliding member 246 to couple sliding member 246 to first guide rail 242 and second guide rail 244, respectively. Similarly, sliding member 247 is slideably coupled to guide rails 243, 245 between an opposite side of sensing assembly frame 238 and mounting member 241. Sliding member 247 includes first guide member 250 and second guide member 251 extending from opposite sides of sliding member 247 to couple sliding member 247 to first guide rail 245 and second guide rail 243, respectively. In some embodiments, one of guide members 248, 249 may be fixedly attached to the corresponding guide rail and the other may be slidably attached to the corresponding guide rail. Similarly one of guide members 250, 251 may be fixedly attached to the corresponding guide rail and the other may be slidably attached to the corresponding guide rail. Since at least one guide member on each side of sensing frame assembly 238 may be slidably coupled with mounting member 241, sensing assembly frame 238 is able to slide with respect to mounting member 241. During operation, sensing assembly frame 238 may slide along guide rails 242, 243 until it is raised to a position where it can be contacted by the sample held in the sample holder. After sample contact, sensing assembly frame 238 is retracted back to the position where it is below the cutting member of the mounting base (see mounting base 111 of FIG. 1).

Figure 3A:
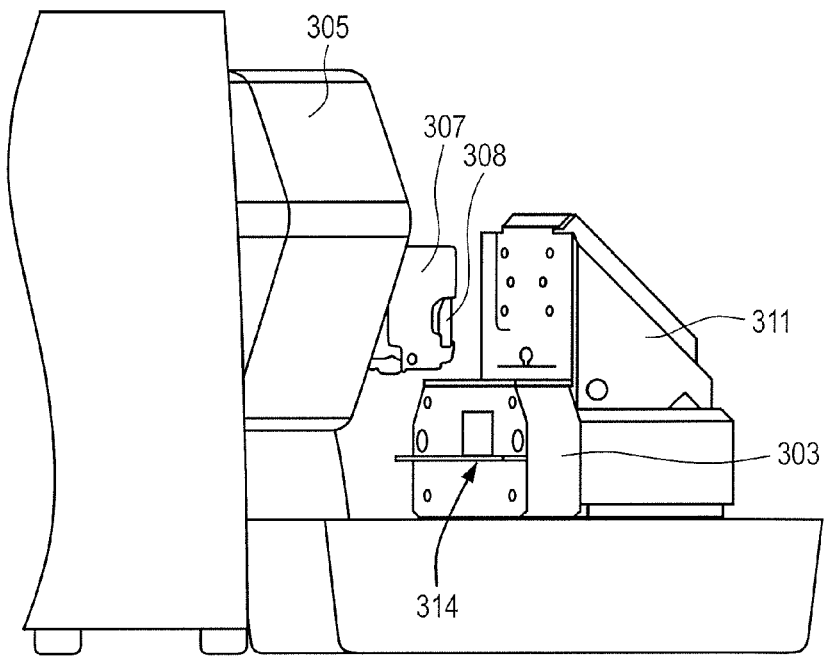
FIG. 3A illustrates an embodiment of a sensor assembly in a retracted position.
Figure 3B:
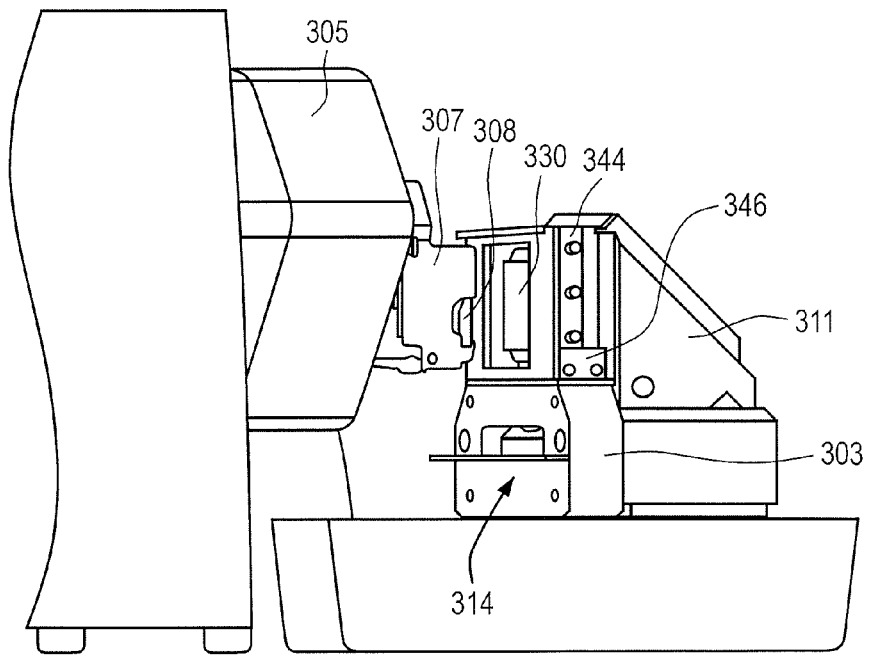
FIG. 3B illustrates an embodiment of a sensor assembly in a raised position.

FIG. 3A and FIG. 3B illustrate embodiments of sensor assembly 314 in a retracted and a raised position, respectively. FIG. 3A illustrates an embodiment of sensor assembly 314 in the retracted position where sensing plate (not shown in this view) and sensing frame (not shown in this view) are retracted below mounting base 311. As shown in FIG. 3A, mounting member 303 is positioned below mounting base 311. During a slicing operation, sensor assembly 314 can be retracted into mounting member 303 so that it does not interfere with the slicing. Sample 308 is shown attached to sample holder 307. Sample holder 307 is attached to vertical drive member 305.

To sense an angular orientation of a surface of sample 308, sensor assembly 314 may be raised vertically so that sensing plate 330 is aligned with sample 308 as illustrated in the embodiment of FIG. 3B. As shown in FIG. 3B, rail member 344 of sensing assembly 314 slides along sliding member 346 to allow sensing plate 330 to be raised above mounting member 303 so that it is positioned in front of mounting base 311. Although not shown, a rail member positioned on an opposite side of sensing assembly 314 may also slide along a corresponding sliding member. Sample 308 is aligned with sensing plate 330 and advanced horizontally in a direction toward sensing plate 330. An angular orientation of the foremost surface of sample 308 can then be detected by pressing the foremost surface of sample 308 against sensing plate 330. The detected angular orientation may be used to facilitate realignment of the angular orientation of foremost surface of sample 308 so that it is parallel, sufficiently parallel, or at least more parallel, to a cutting member and/or cutting plane. If desired, multiple such sensing measurements may be made at different times or repeatedly throughout the realignment process, or alternatively a single measurement and single adjustment based on that single measurement may be made. Then, sensor assembly 314 may be lowered below mounting base 311 as illustrated in FIG. 3A to prepare the microtome for a sectioning operation.

Refer again to FIG. 1, and notice that in this illustrated embodiment, sensor assembly 114 is positioned horizontally between support member 115 and cutting member 112 and/or cutting plane 124. Sensor assembly 114 is operable to move vertically up and down as viewed. One aspect associated with positioning sensor assembly 114 horizontally between support member 115 and cutting member 112 is that sample 108 may need to traverse a greater horizontal distance in the direction of horizontal arrow 125 to reach cutting member 112 and/or cutting plane 124 due in part to extra horizontal distance to accommodate a width dimension of sensor assembly 114, for example the dimension "w" shown in FIG. 1, which may be on the order of 3 cm. The traversal of the greater horizontal distance may take additional time, which depending upon the implementation may be undesired. For example, commonly the movement in the horizontal direction is relatively slower than in the vertical direction. This may be a result of a desire to provide a finer accuracy of movement in the horizontal direction in order to provide accurate horizontal positions to achieve accurate control over sectioning thickness.

Alternate embodiments are contemplated where sensor assembly 114 is not horizontally disposed between sample 108 and/or support member 115 and cutting mechanism 112. For example, in some embodiments, sensor assembly 114 may be in a fixed positioned approximately vertically below cutting member or mechanism 112 and/or cutting plane 124. One potential advantage to positioning sensor assembly 114 vertically below cutting member 112 is that sample 108 may not need to traverse additional distance (e.g., on the order of 3 cm) in the horizontal direction of arrow 125 to reach cutting member 112 and/or cutting plane 124. This may help to reduce the amount of time for sample to move horizontally to cutting member 112. In some embodiments, vertical movement of vertical drive member 105 may be relatively faster than horizontal movement of horizontal drive member 106. Vertical drive member 105 may move down an additional distance (e.g., on the order of 64 cm) in the direction of vertical arrow 126 to reach sensor assembly 114. In some cases, it may take less time for vertical drive member 105 to travel the extra distance in the vertical direction to reach sensor assembly 114 below cutting mechanism 112 than it would take for horizontal drive member 106 to travel the extra distance in the horizontal direction due to the width of sensor assembly 114. This may help to speed up the time to sense surface orientations and adjust the surface orientations.

As previously discussed, an initial position of the foremost surface of the sample may be detected by pressing the sample against the sensing plate. Based on the degree of rotation of the sensing plate and the sensing frame about their respective axis, an angular orientation and position of the surface of the sample can be determined. The various axis and rotation of the sensing plate and sensing frame about their axis are illustrated in the embodiments of FIGS. 4A, 4B, 4C and 4D.

Figure 4A:
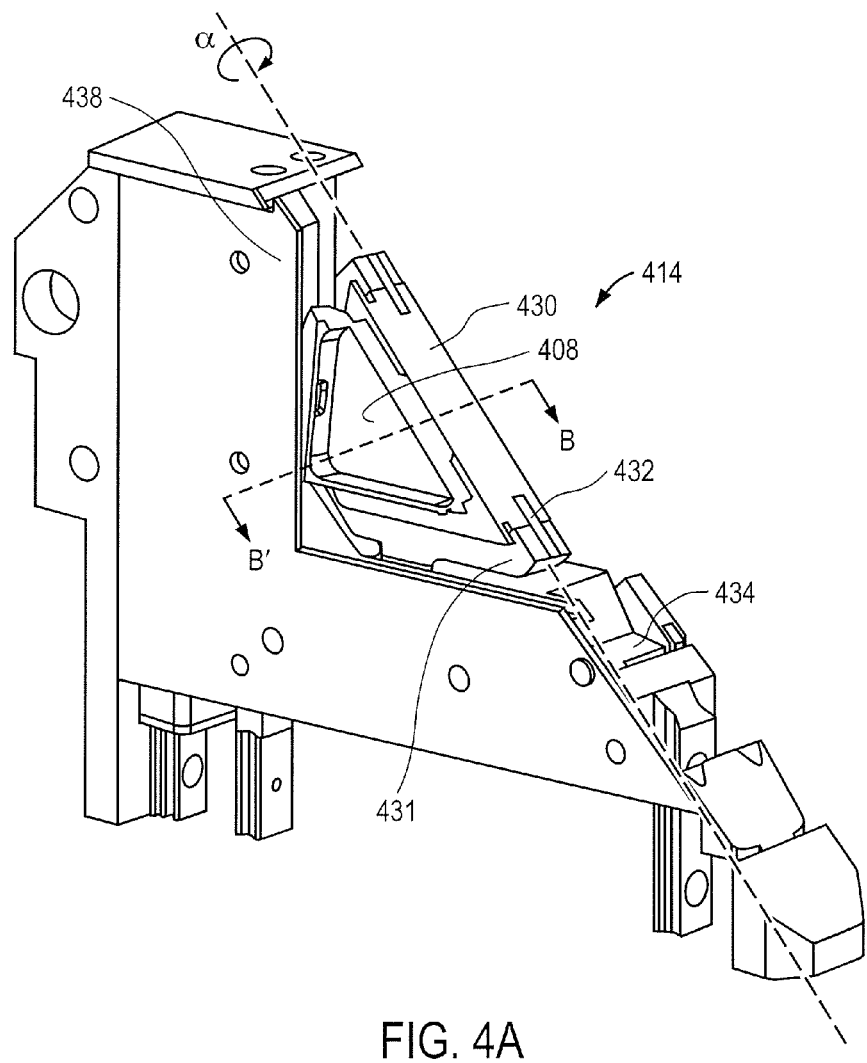
FIG. 4A illustrates a cut out perspective view of an embodiment of a sensor assembly having a first axis of a sensing plate.
Figure 4B:
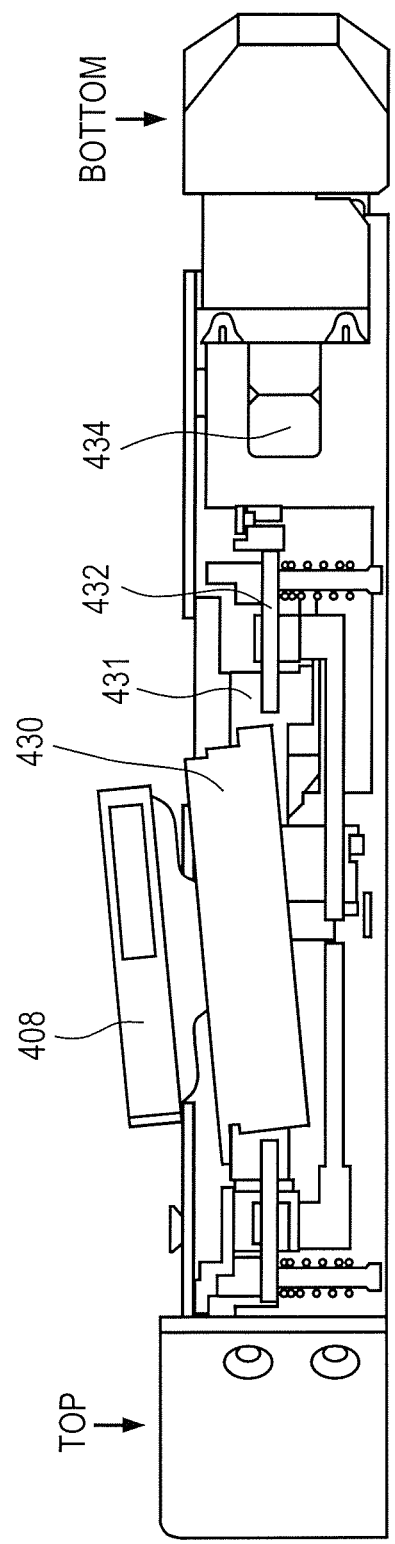
FIG. 4B illustrates a cross sectional view of an embodiment of the sensor assembly of FIG. 4A along section line B-B'.

FIG. 4A illustrates a cut out perspective view of an embodiment of sensor assembly 414 having a first axis of a sensing plate. FIG. 4B illustrates a cross sectional view of an embodiment of sensor assembly 414 of FIG. 4A along line B-B'. In this aspect, sensor assembly 414 includes sensing plate 430 and sensing frame 431 attached to sensing assembly frame 438. First axial support member 432 is positioned diagonally through sensing plate 430 to provide a first axis of rotation for sensing plate 430 at an angle of rotation ($\alpha$). A second axial support member 433 (shown in FIG. 4D) is positioned diagonally though sensing frame 431 to provide a second axis of rotation for sensing frame 431. The second axis of rotation is substantially perpendicular to the first axis of rotation (for example 80-100 degrees).

During operation, a foremost or cutting surface of sample block 408 (e.g., a tissue sample embedded in a paraffin block or cassette) is pressed against sensing plate 430. In some cases, the surface of sample block 408 is not parallel to a cutting member and/or cutting plane. Pressing the surface of sample block 408 against sensing plate 430 causes rotation of sensing plate 430 along first axial support member 432 as illustrated in FIG. 4B so that sensing plate 430 conforms to an angular orientation of the surface of sample block 408. The degree of rotation of sensing plate 430 along first axial support member 432 is detected by sensing plate sensor 430 attached to sensing assembly frame 438. This information is then used in part to determine the angular orientation of the surface of sample block 408.

Figure 4C:
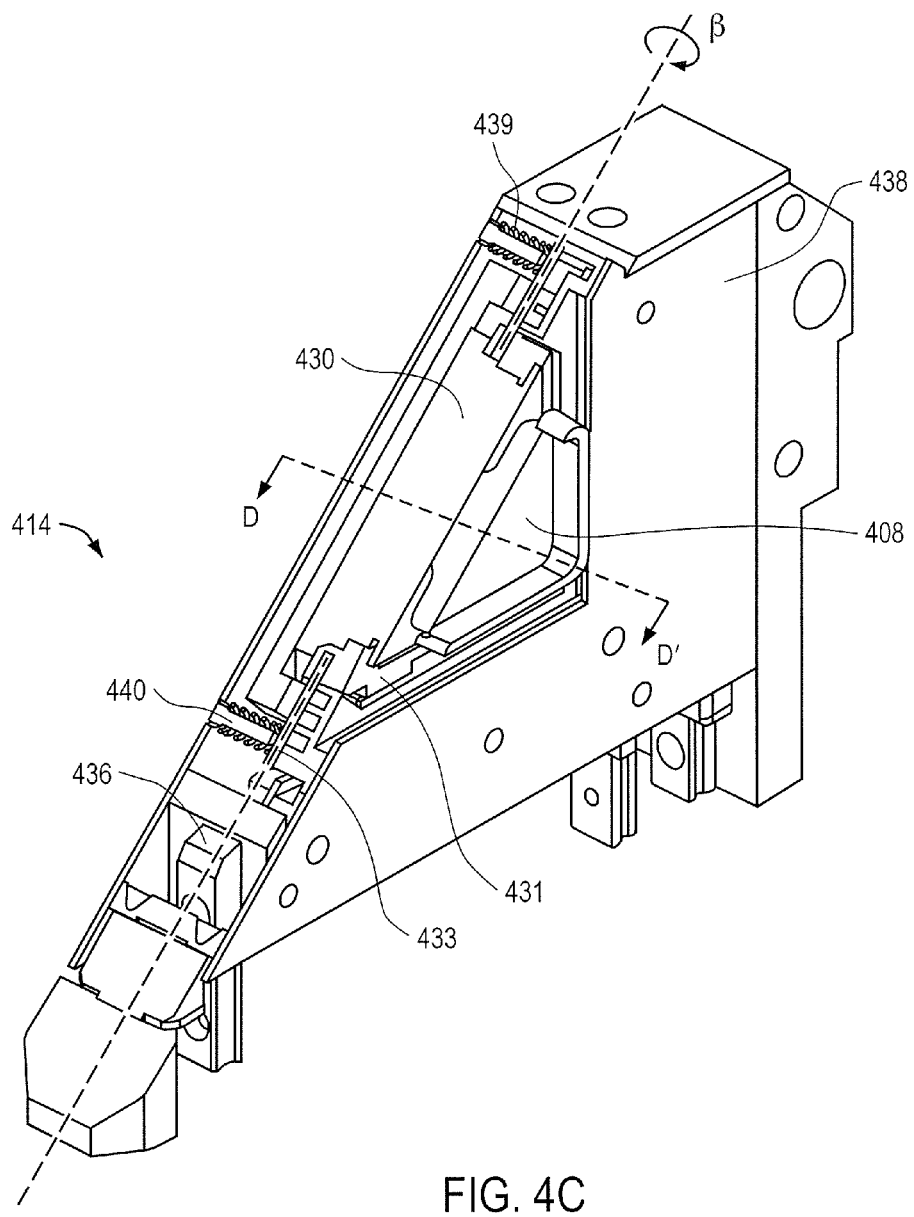
FIG. 4C illustrates a cut out perspective view of an embodiment of a sensor assembly having a sensing frame with a second axis of rotation about a second axial support member.
Figure 4D:
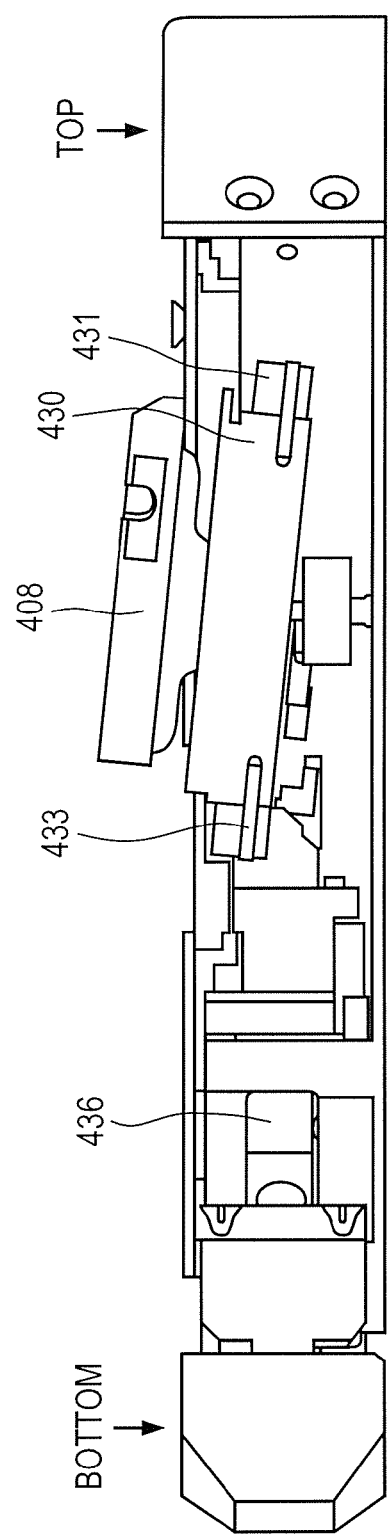
FIG. 4D illustrates a cross sectional view of an embodiment of the sensor assembly of FIG. 4C along section line D-D'.

In addition to rotating sensing plate 430, the angled surface of sample block 408 may cause rotation of sensing frame 431 along second axial support member 432 illustrated in FIGS. 4C and 4D. FIG. 4C illustrates a cut out perspective view of an embodiment of a sensor assembly 414 having sensing frame 431 with a second axis of rotation about second axial support member 433. Sensing frame 431 may rotate about the second axis of rotation at an angle ($\beta$). FIG. 4D illustrates a cross sectional view of an embodiment of sensor assembly 414 of FIG. 4C along line D-D'. As previously discussed, second axial support member 433 is positioned diagonally through sensing frame 431 and substantially perpendicular to first axial support member 432 (for example 80-100 degrees). As such, when the surface of sample block 408 is angled with respect to second axial support member 433, sensing frame 431 will rotate about second axial support member 433 as illustrated in the embodiment of FIG. 4D. The degree of rotation may be detected by sensing frame sensor 436 attached to sensing assembly frame 438. This information may be combined with the information relating to the degree of rotation of sensing plate 430 to determine the angular orientation of the foremost or cutting surface of sample block 408.

First biasing member 439 and second biasing member 440 to allow movement of sensing frame 431 in a horizontal direction (e.g., the direction of horizontal double arrow 125 in FIG. 1) are further illustrated in FIG. 4C. First biasing member 439 and second biasing member 440 may be positioned along opposite ends of second axial support member 433 to bias second axial support member 433 in a horizontal direction towards of sample block 408. In some embodiments, first biasing member 439 and second biasing member 440 may be springs, pneumatic cylinders, or the like. Pressing sample block 408 against sensing plate 430 forces second axial support member 433 against first biasing member 439 and second biasing member 440 to allow for retraction of sensing plate 430 and sensing frame 431 in a horizontal direction (e.g., the direction of horizontal double arrow 125 in FIG. 1) away from sample block 408. In some embodiments, the degree of movement in this direction may optionally be detected using an optional sensor, for example an optical sensor, mechanical sensor, magnetic field sensor, or the like, positioned at each end of second axial support member 433. The optical sensors may detect a degree of movement of second axial support member 433 in the horizontal direction away from sample block 408. This horizontal displacement information may be used in addition to the information relating to the amount of rotation of sensing plate 430 and sensing frame 431 to determine not only an angular orientation of the foremost surface of sample block 408 but also a horizontal position of the foremost surface of sample block 408. Advantageously, knowing the horizontal position of the foremost surface of sample block 408 may help to achieve a cut of an intended thickness.

To further illustrate certain concepts, consider a specific non-limiting embodiment by which both an angular orientation of a foremost surface of sample block 408 and a horizontal position of foremost surface of sample block 408 may be determined. In this example embodiment, sensing plate 430 and sensing frame 431 may each detect an angle of the surface of sample block 408 (with respect to the cutting plane) of up to about five degrees (for example), along their respective axis. In particular, sensing plate 430 may rotate about first axial support member 432 up to about five degrees (5°) from an initial position parallel to the cutting plane. Similarly, sensing frame 431 may rotate about second axial support member 433 up to about five degrees (5°) from an initial position parallel to the cutting plane. Pressing the surface of sample block 408 against sensing plate 430 may cause sensing plate 430 and/or sensing frame 431 to rotate to a degree equivalent to the degree to which the surface of sample block 408 is offset from the cutting plane. Sensing plate 430 and sensing frame 431 may detect a combined angle of up to about seven degrees (7°), in this particular embodiment, to determine an overall angular orientation that the surface of sample block 408 is offset from the cutting plane.

Once the angular orientation is determined, the microtome may autonomously determine an adjustment, and autonomously adjust the angular orientation of the surface of the sample block 408 by the determined adjustment, so that it is parallel, substantially parallel, or more parallel relative to cutting member and/or cutting plane. For example, if it is determined that the surface of sample block 408 is offset from the cutting plane at a total angle of approximately four degrees (4°), then the surface of sample block 408 may be rotated approximately four degrees (4°) in the opposite direction so that the surface of sample block 408 is approximately parallel to the cutting plane. If desired, multiple sensing measurements may be made while the angle is gradually decreased in small adjustments. It is to be understood that other embodiments may utilize either greater or lesser degrees of rotation than the particular degrees of rotation described for this example embodiment. In addition, the horizontal position of foremost surface of sample block 408 may be detected using a sensor to sense the horizontal movement of sensing frame 431 when sample block 408 is pressed against sensing plate 430. Knowing the horizontal position of the foremost surface of sample block 408 may allow microtome to make initial cuts of a desired thickness.

Sensor assemblies 214, 314, and 414 shown in FIG. 2, FIGS. 3A-3B, and FIGS. 4A, 4B, 4C, and 4D, respectively, represent example embodiments of suitable surface orientation sensors. However, other surface orientation sensors are also contemplated. Some of these alternate surface orientation sensors are contact-based sensors or sensor assemblies analogously to sensor assemblies 214, 314, and 414 described above. However, they may make use of different contact-based sensing mechanisms for sensing the orientation of the surface of the sample. For example, in one alternate embodiment, rather than using a sensing frame, a sensing plate may be mounted on a single pivot (for example a ball joint), which allows the sensing plate to rotate in two dimensions to conform to an orientation of the cutting surface of the sample. Still other contemplated surface orientation sensors are non-contact-based sensors that need not contact the surface of the sample to determine an orientation of the surface of the sample. For example, in one embodiment, an optical sensing system may optically sense the orientation of the surface of the sample, for example by directing or scanning one or more laser beams onto the surface. Other approaches may be based on acoustics, interferometry, etc.

Sample holders capable of realigning an orientation of a surface of a sample so that they are parallel or more parallel with a cutting member and/or a cutting plane are known in the arts. In some embodiments, the feed drive system may have a multi-axis workpiece chuck or motorized chuck that is capable of adjusting an orientation of the cutting surface of the sample in two dimensions relative to a cutting member and/or cutting plane. Examples of suitable multi-axis workpiece chucks are described in U.S. Pat. No. 7,168,694, entitled "MULTI-AXIS WORKPIECE CHUCK," by Xuan S. Bui et al., filed on Jan. 22, 2004, and assigned to the assignee of the present application. In one embodiment, the multi-axis chuck may have a mounting assembly that retains a workpiece, such as a sample, in a substantially fixed orientation with respect to the chuck. The chuck may be motor-driven and may be rotatable about at least two axes which may be perpendicular. The chuck may be rotated manually by an operator using a controller that is in communication with one or more motors, or the microtome may autonomously rotate the chuck. One or more sensors may be used to sense a position of the chuck. According to one embodiment, each axis may have three sensors that detect a middle nominal position and end positions of the chuck. A user or the microtome may control movement of the chuck by signaling the motor to rotate the chuck to the desired position. The sensors may be used to determine whether the desired position has been reached. In one embodiment, the chuck may include first and second portions that are rotatable about at least two orthogonal axes. The first portion may rotate about a first axis and independently of the second portion. Rotation of the second portion about a second axis may cause the first portion to rotate about the second axis also. This may allow the chuck to be rotatable in multiple dimensions.

In some embodiments, a locking mechanism may also optionally be provided. After rotating the multi-axis chuck, a locking mechanism may be engaged to lock the multi-axis chuck in the desired position. This locking mechanism may be, for example, a permanent magnet solenoid, a geared motor or a rotating handle that causes the first, second, and third portions to lock by friction or other known manner. In one embodiment, a motor may be used to tighten the chuck at times when the chuck is not being adjusted. When the microtome determines to adjust the position of the sample by adjusting the chuck, or when a user decides to manually adjust the position of the tissue sample by adjusting the chuck, the motor may be signaled to loosen the chuck to allow the chuck to be adjusted. At other times, when the position of the chuck is not being adjusted, the motor may be signaled to maintain the chuck in a tightened or locked configuration so that the position of the chuck and/or the position of a sample held by the chuck do not change unintentionally.

In some embodiments, a sectioning cycle may include: (1) moving sample block 408 in a forward horizontal direction toward the cutting plane a predetermined distance related to the desired slice thickness; (2) moving sample block 408 in a vertical direction (for example downward) toward the cutting member to obtain a slice; (3) moving the sample block 408 in a backward or opposite horizontal direction away from the cutting plane and/or cutting member a predetermined distance; and (4) moving sample block 408 in an opposite vertical direction (for example upward) away from the cutting member. Retracting or moving the sample block 408 in a backward horizontal direction away from the cutting member helps to avoid sample block 408 contacting the cutting member during (4) when moving sample block 408 in the opposite vertical direction (for example upward) away from the cutting member. Representatively, the distance sample block 408 is retracted may correspond to a thickness of the sliced sample. Alternatively, it is contemplated that in some embodiments, the retraction step may be omitted. The slicing cycle may be repeated until a desired number of slices are obtained.

In some embodiments, a microtome may be capable of using different speeds of movement of a feed drive system and/or a sample (e.g., sample block 410 in FIG. 4A or sample 108 in FIG. 1) for different portions of a sectioning cycle. For example, in some embodiments, a relatively faster speed of movement of the feed drive system and/or a sample may be used during one or more non-sectioning portions of a sectioning cycle (e.g., where cutting or sectioning of a sample is not performed), whereas a relatively slower speed of movement of the feed drive system and/or a sample may be used during a sectioning portion of the sectioning cycle (e.g., where cutting or sectioning of the sample is performed). Using a relatively slower speed of movement of the feed drive system and/or sample during cutting or sectioning of the sample tends to provide higher quality sections and/or more consistent sections, whereas performing one or more other non-sectioning portions of the sectioning cycle more rapidly may help to improve the overall speed of the sectioning cycle and/or may allow more sections to be produced in a given amount of time. As such, the speed of movement of a feed drive system and/or a sample may vary throughout a sectioning cycle. For example, a user may control or program a sectioning cycle so that movement of sample block 410 or sample 108 in a vertical direction (for example downward) toward the cutting member to obtain a slice (e.g., operation (2) in the paragraph above) is performed more slowly than one or more other portions of the sectioning cycle (e.g., operations (1), (3), (4), or a combination thereof, in the paragraph above).

In some embodiments, a microtome may include logic to allow a configurable or programmable sectioning portion of a sectioning cycle to be specified over which relatively slower speed of movement of the feed drive system and/or a sample are to be used. For example, in some embodiments, the microtome may include logic to allow a configurable or programmable sectioning length to be configured or programmed. By way of example, the length may be selected from among a plurality of predetermined lengths corresponding to different types of cassettes having different dimensions. Different types of cassettes have different sectioning lengths over which sectioning is performed. As one example, 7019 Paraform® brand Biopsy 13 mm×13 mm Cassettes, and 7020 Paraform® brand Biopsy 26 mm×19 mm Cassettes, which are commercially available from Sakura Finetek USA, Inc., of Torrance, Calif., have different sectioning lengths. In one example embodiment, the microtome may be operable to allow an operator to specify or indicate a sectioning length. The specification or indication of the sectioning length may be done in different ways, such as, for example, by specifying a length, selecting a length from among a plurality of predetermined lengths, specifying a type of cassette, selecting a type of cassette from among a plurality of different types of cassettes, etc. For example, when a user is ready to product sections from a particular type of cassette, the user may make a selection of the particular type of cassette using a control device (e.g., control device 116 in FIG. 1), and the microtome may already be preprogrammed with a predetermined sectioning length corresponding to that particular type of cassette. During sectioning, the microtome may use a relatively slower speed of movement of the feed drive system and/or the sample over the specified sectioning length and may use relatively faster speeds of movement over one or more or substantially all other portions of the sectioning cycle. For example, immediately or just before and immediately or just after the cutting of the sample over the specified sectioning length the relatively faster speeds may be used.

In some embodiments, a microtome may include logic to initially autonomously remove a given or predetermined portion of a sample (e.g., sample 108 in FIG. 1 or sample block 408 in FIG. 4A). For example, the portion may include a given or predetermined thickness of paraffin, embedding material, cassette material, or other non-tissue material overlying or concealing the actual tissue material from which a section is desired to be taken (e.g., disposed between a cutting surface of the tissue material and the foremost external surface of the sample which would contact a sensing plate). By way of example, a sample may include a piece of tissue placed on a bottom of a cassette and the cassette and the tissue sample embedded in a block of embedding material. In the case of various cassettes manufactured by Sakura Finetek USA, Inc., of Torrance, Calif., the cassettes may include a Paraform® brand cassette material that has sectioning characteristics similar to that of paraffin and sectioning may be performed through the Paraform® brand cassette material of the cassette bottom.

In some embodiments, a microtome may include logic to initially autonomously remove a given or predetermined portion of a sample, for example, a portion of paraffin, embedding material, cassette material, or other non-tissue material overlying or concealing an actual tissue material desired to be sectioned. For example, the microtome may autonomously remove a bottom of a cassette in order to expose or provide access to the actual tissue material of the sample. Representatively, in the case of certain cassettes, depending upon the thickness of the material making up the bottom of the cassette and the thickness of the sections, the microtome may autonomously make a plurality (e.g., from around two to about twenty, often from about five to about fifteen) of sections to remove a predetermined thickness of the bottom of the cassette. The thickness of the bottom of the cassette may be known by the microtome or predetermined. For example, a user may specify the thickness directly, or select a type of cassette from among several different types that each has a preprogrammed or otherwise known cassette bottom thickness. In some cases, the operator may control the microtome to perform the automated process, for example, with a user input device (e.g., a trim button) on a control device or otherwise selecting a trim operation. Advantageously, allowing the microtome to autonomously remove the portion of the sample (e.g., the bottom of the cassette) may relive the operator from having to do so and/or may tend to speed up the removal of the portion of the sample (e.g., the bottom of the cassette). Then, once the actual tissue of the sample is exposed, a sectioning cycle to obtain slices or sections of the tissue may be commenced (e.g., the operator may press a section button or otherwise cause the microtome to take a section from the now exposed cutting surface of the tissue sample.

Figure 5:
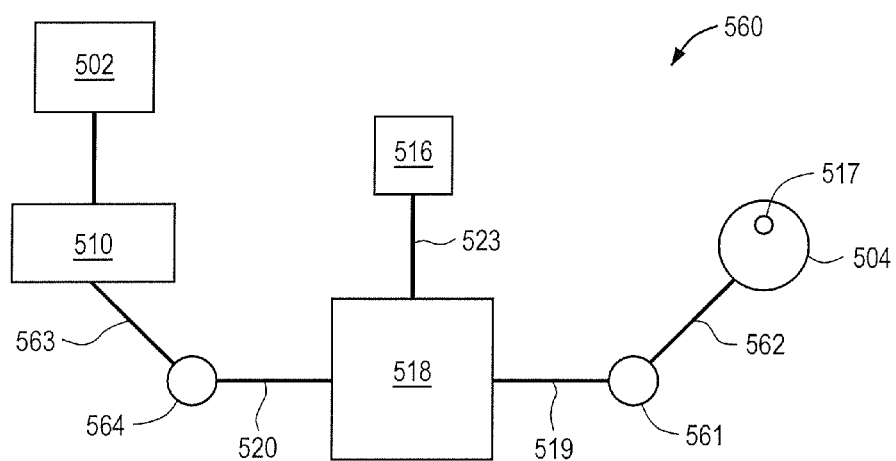
FIG. 5 illustrates an embodiment of a control system for controlling an operation of a microtome including a handwheel and control device.

As previously discussed, the slicing operation may proceed automatically or manually through user interaction with the system. FIG. 5 illustrates an embodiment of a control system for controlling an operation of the microtome including a handwheel and control device. Control system 560 may include handwheel 504 and control device 516. Handwheel 504 may include handle or other pulse generating device 517 to lock handwheel 504. In some embodiments, handwheel 504 is coupled to motor 510 using a non-mechanical coupling or non-mechanical mechanism (for example an electrical coupling). Typically, microtomes include a handwheel that is mechanically coupled to the motor. Such mechanical coupling, however, adds resistance to the handwheel when the user tries to turn it. Repeated turning of such a handwheel can be taxing on the user and may at times result in medical conditions such as carpal tunnel syndrome. The non-mechanical coupling or mechanism disclosed herein may offer the advantage of reduced handwheel resistance resulting in a handwheel that is easier to turn.

In some embodiments, the non-mechanical coupling or mechanism includes first encoder 561. First encoder 561 may be a rotary encoder coupled to shaft 562 of handwheel 504. Rotation of handwheel 504 and in turn shaft 562 provides first encoder 561 with an angular position of handwheel 504. First encoder 561 then converts the angular position to an electrical representation (for example an analog or digital code or value). This analog or digital code is transmitted to control circuit 518 via control line 519 where it is processed and used to direct movement of motor 510 and in turn feed drive 502. In some embodiments, motor 510 having feed drive 502 coupled thereto may be connected to control circuit 518 by second encoder 564. In this aspect, shaft 563 of motor 506 may be connected to second encoder 564 so that second encoder 564 may detect a position of motor 510 during the cutting operation. Encoder 564 then converts this position information to an electrical representation (for example an analog or digital code or value) and transmits the electrical representation to control circuit 518 via control line 520. In some embodiments, control circuit 518 may control the motor based at least in part on the electrical representation of the angular position of the handwheel. For example, since positions of both handwheel 504 and motor 510 are known, control circuit 518 can ensure that the position of handwheel 504 corresponds to, and is in alignment with, the position of motor 510 during a cutting operation. For example, rotation of handwheel 504 may not cause movement of motor 510 until a comparison of signals from the respective first and second encoders indicate that a position of handwheel 504 is aligned with a position of drive shaft of motor 510. This may tend to increase safety of operation of the microtome, especially when transferring from an automated mode of sectioning to a manual mode of sectioning.

Control device 516 may further be operable to initiate an automated cutting operation. Control device 516 may be any type of input device suitable for initiating a cutting operation. Representatively, control device 516 may include, for example, a keyboard, a keypad, a capacitive sensor touch pad, or other user data input device. In some embodiments, signals are transmitted between control device 516 and control circuit 518 via control line 523. In other embodiments, control device 516 may be a wireless control device that is operable to transmit wireless control signals to control circuit 518 and optionally receive wireless signals from control circuit 518. The control line 523 may be omitted. Wireless control device 516 may have a wireless transmitter, wireless receiver, and/or wireless transceiver, a wireless protocol stack, and other conventional components found in wireless devices. In one aspect, wireless control device 516 may be a Bluetooth capable device, although this is not required.

Control device 516 may include keys or simulated keys that can be used to control the actions of the microtome. Representatively, the keys may present graphic symbols or text corresponding to the various operations of the microtome, such as arrows corresponding to a vertical or horizontal movement of the microtome and/or other words, symbols, pictures, or the like, corresponding to, for example, slicing, stop, start, trim a bottom of a cassette, section, locking, or other microtome operations. The user selects the operation to be performed using the control device 516 and pushes the appropriate key(s) to initiate the desired operation. The control signal is transmitted from control device 516 to control circuit 518. Control circuit 518 then provides a signal to, for example, motor 510 to initiate a cutting operation. The cutting operation may then continue automatically or autonomously substantially without additional user intervention until the user either presses a stop key or a preprogrammed cutting operation is completed.

Figure 6:
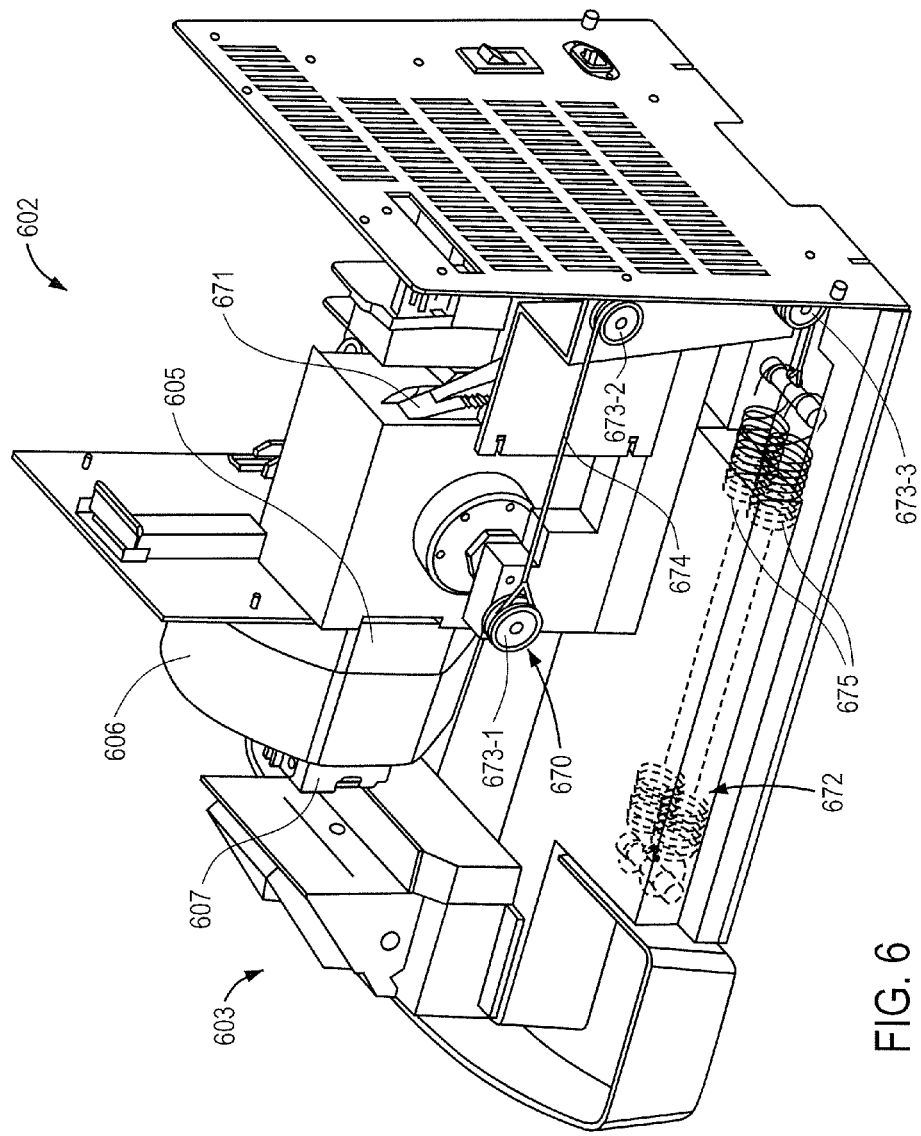
FIG. 6 illustrates a perspective view of an embodiment of a feed drive system of a microtome.

FIG. 6 illustrates a perspective view of an embodiment of a feed drive system of a microtome. In one embodiment, feed drive system 602 may be used for feed drive system 102 described in reference to FIG. 1. Alternatively, feed drive system 102 may use an entirely different feed drive system than feed drive system 602. Feed drive system 602 includes vertical drive member 605, horizontal drive member 606 and sample holder 607. Mounting member 603 for holding a cutting member may further be positioned in front of sample holder 607. In one embodiment, mounting member 603 may be substantially similar to mounting member 103 described in reference to FIG. 1.

During operation, vertical movement of feed drive system 602 is achieved by moving a slider (not shown) of vertical drive member 605 vertically along a track. Movement of the slider is caused by rotating pin (not shown) attached to a rotating plate (not shown) which is turned by driving belt 671 and motor (not shown). To reduce the load on the motor, the weight of feed drive system 602 may be counter-balanced. For example, in one embodiment, the weight may be counterbalanced using spring assembly 672 instead of a counterweight. Counterweights tend to be heavy and tend to increase the weight and cost of the microtome. Alternatively, a counterweight may be used if desired. Spring assembly 672 may include pulleys 673-1, 673-2, 673-3. Pulley 673-1 may be attached to pin 670. Cable 674 may be attached at one end to pulley 673-1, extend around pulleys 673-2 and 673-3 and be attached at the opposite end to springs 675. In this aspect, as feed drive system 602 is moved vertically, springs 675 exert a counter-balancing force on cable 674, which in turn pulls on pin 670 and counters the weight of feed drive system 602. Spring assembly 672 may help to reduce the weight of the system by eliminating a counterweight and may help to reduce the inertia load on the motor. Although spring assembly 672 is described in one embodiment, it is further contemplated that in other embodiments, a half-circle heavy mass attached to pin 670 may be used to counter-balance feed drive system 602. Although a half-circle heavy mass is also effective at counter-balancing feed drive system 602, it tends to increase the inertia load to the motor.

In some embodiments, a microtome may optionally include a lock that is operable to lock a feed drive system (e.g., feed drive system 104 in FIG. 1 or feed drive system 602 in FIG. 6) in a vertical position. As one example, the lock may include a spring biased disc brake. The spring biased disc brake may include a disc brake, a pin or other locking member, and one or more springs or other mechanical biasing elements to bias the pin or other locking member into a locking engagement with the disc brake when a deliberate unlock signal is not applied. Other types of locks known in the arts are also suitable, such as, for example, a pin or other locking member biased into a hole. The lock may hold the feed drive system in a fixed, locked vertical position when the lock is not deliberately disabled. At appropriate times, when movement of the feed drive system is desired, an unlock signal (e.g., an electrical signal) may be deliberately applied to the lock, to open the lock (e.g., compress the spring, which may unlock the disc brake). Advantageously, such a lock may help to prevent or at least reduce the likelihood that an operator is harmed due to a moving or falling feed drive system, for example in the event of a power failure or otherwise. Without such a lock, the operator may be damaged by the blade or other cutting member if the feed drive system were to fall or move unexpectedly.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment.

In the foregoing specification, the invention has been described with reference to specific embodiments thereof. It will, however, be evident that various modifications and changes can be made thereto without departing from the broader spirit and scope of the invention as set forth in the appended claims. The specification and drawings are, accordingly, to be regarded in an illustrative rather than a restrictive sense.

In the description above, for the purposes of explanation, numerous specific details have been set forth in order to provide a thorough understanding of the embodiments of the invention. It will be apparent however, to one skilled in the art, that one or more other embodiments may be practiced without some of these specific details. The particular embodiments described are not provided to limit the invention but to illustrate it. The scope of the invention is not to be determined by the specific examples provided above but only by the claims below. In other instances, well-known circuits, structures, devices, and operations have been shown in block diagram form or without detail in order to avoid obscuring the understanding of the description.

It will also be appreciated, by one skilled in the art, that modifications may be made to the embodiments disclosed herein, such as, for example, to the sizes, shapes, configurations, couplings, forms, functions, materials, and manner of operation, and assembly and use, of the components of the embodiments. All equivalent relationships to those illustrated in the drawings and described in the specification are encompassed within embodiments of the invention. Further, where considered appropriate, reference numerals or terminal portions of reference numerals have been repeated among the figures to indicate corresponding or analogous elements, which may optionally have similar characteristics.

Various operations and methods have been described. Some of the methods have been described in a basic form, but operations may optionally be added to and/or removed from the methods. In addition, while a particular order of the operations according to example embodiments has been described, it is to be understood that that particular order is exemplary. Alternate embodiments may optionally perform the operations in different order, combine certain operations, overlap certain operations, etc. Many modifications and adaptations may be made to the methods and are contemplated.

One or more embodiments include an article of manufacture (e.g., a computer program product) that includes a machine-accessible and/or machine-readable medium. The medium may include, a mechanism that provides (e.g., stores) information in a form that is accessible and/or readable by the machine. The machine-accessible and/or machine-readable medium may provide, or have stored thereon, a sequence of instructions and/or data structures that if executed by a machine causes or results in the machine performing, and/or causes the machine to perform, one or more or a portion of the operations or methods disclosed herein. In one embodiment, the machine-readable medium may include a tangible non-transitory machine-readable storage media. For example, the tangible non-transitory machine-readable storage media may include a floppy diskette, an optical storage medium, an optical disk, a CD-ROM, a magnetic disk, a magneto-optical disk, a read only memory (ROM), a programmable ROM (PROM), an erasable-and-programmable ROM (EPROM), an electrically-erasable-and-programmable ROM (EEPROM), a random access memory (RAM), a static-RAM (SRAM), a dynamic-RAM (DRAM), a Flash memory, a phase-change memory, or a combinations thereof. The tangible medium may include one or more solid or tangible physical materials, such as, for example, a semiconductor material, a phase change material, a magnetic material, etc.

It should also be appreciated that reference throughout this specification to "one embodiment", "an embodiment", or "one or more embodiments", for example, means that a particular feature may be included in the practice of the invention. Similarly, it should be appreciated that in the description various features are sometimes grouped together in a single embodiment, Figure, or description thereof for the purpose of streamlining the disclosure and aiding in the understanding of various inventive aspects. This method of disclosure, however, is not to be interpreted as reflecting an intention that the invention requires more features than are expressly recited in each claim. Rather, as the following claims reflect, inventive aspects may lie in less than all features of a single disclosed embodiment. Thus, the claims following the Detailed Description are hereby expressly incorporated into this Detailed Description, with each claim standing on its own as a separate embodiment of the invention.

What is claimed is:

1. A sample sectioning device comprising:
    a cutting mechanism that is operable to cut sections from a sample;
    a sample holder that is operable to hold the sample;
    a drive system coupled with the sample holder, the drive system operable to drive movement between the sample held by the sample holder and the cutting mechanism; and
    a surface orientation sensor that is operable to sense an orientation of a surface of the sample held by the sample holder,
    wherein the surface orientation sensor is capable of rotating in two dimensions.

2. The sample sectioning device of claim 1, wherein the surface orientation sensor comprises a first member that is capable of rotating about a first axis and a second member that is capable of rotating about a second axis, and wherein the first axis is substantially perpendicular to the second axis.

3. The sample sectioning device of claim 2, wherein the first member comprises a plate and the second member comprises a frame coupled with the plate.

4. The sample sectioning device of claim 2, further comprising:
    a first sensing mechanism configured to sense rotation of the first member about the first axis; and
    a second sensing mechanism configured to sense rotation of the second member about the second axis.

5. The sample sectioning device of claim 2, wherein the first member and the second member are moveably coupled with the surface orientation sensor and capable of moving in a direction away from the sample when the sample exerts force on one or more of the first and second members.

6. The sample sectioning device of claim 5, further comprising a sensing mechanism configured to sense an amount of movement of the first and second members in the direction away from the sample.

7. The sample sectioning device of claim 1, further comprising:
    a motorized chuck coupled with the sample holder, the motorized chuck capable of adjusting the orientation of the surface of the sample; and logic to cause the sample sectioning device to autonomously adjust the orientation of the surface of the sample based on the sensed orientation.

8. The sample sectioning device of claim 7, wherein the logic comprises logic to cause the sample sectioning device to autonomously adjust the orientation of the surface of the sample relative to a cutting plane associated with the cutting mechanism a plurality of times while adjusted orientations of the surface of the sample are sensed by the surface orientation sensor in order to make the orientation of the surface of the sample more parallel with the cutting plane.

9. The sample sectioning device of claim 7, further comprising a motor of the motorized chuck that is operable to lock a position of the motorized chuck to hold an orientation of the surface of the sample held by the sample holder in a fixed orientation.

10. The sample sectioning device of claim 1, wherein the surface orientation sensor is fixedly coupled with the sample sectioning device at a position, and wherein the position is substantially vertically aligned with the cutting mechanism.

11. The sample sectioning device of claim 1, wherein the surface orientation sensor is moveably coupled with the sample sectioning device, the surface orientation sensor operable to move between a first position where the surface orientation sensor is positioned to sense the orientation of the surface of the sample held by the sample holder and a second retracted position farther away from the movement between the sample held by the sample holder and the cutting mechanism.

12. The sample sectioning device of claim 1, further comprising:
a handwheel;
a first encoder coupled with the handwheel by a first shaft, the first encoder operable to generate an electrical representation of an angular position of the handwheel;
a motor of the drive system;
a second encoder coupled with the motor of the drive system by a second shaft, the second encoder operable to generate an electrical representation of an angular position of the motor of the drive system; and
a control circuit electrically coupled with the first and second encoders and operable to receive the electrical representations of the angular positions of the handwheel and the motor, the control circuit operable to control the motor based at least in part on the electrical representation of the angular position of the handwheel.

13. The sample sectioning device of claim 12, wherein the control circuit is operable to control the motor not to move until a comparison of the electrical representations of the angular positions of the handwheel and the motor indicate that a position of the handwheel is aligned with a position of the motor.

14. The sample sectioning device of claim 1, further comprising logic to allow a configurable sectioning length to be specified, wherein the sample sectioning device is to move the sample at a relatively slower speed of movement during the specified sectioning length and at a relatively faster speed of movement during at least one of just before and just after the movement during the specified sectioning length.

15. The sample sectioning device of claim 14, wherein the logic comprises logic to allow an operator to select the sectioning length from among a plurality of predetermined sectioning lengths each corresponding to a different type of cassette used to hold the sample.

16. The sample sectioning device of claim 14, wherein the logic comprises logic to allow an operator to specify the sectioning length by selecting one of a plurality of different types of cassettes.

17. The sample sectioning device of claim 1, further comprising logic to cause the sample sectioning device to autonomously remove a given thickness of the sample concealing a tissue within the sample, the given thickness associated with a thickness of a bottom of a cassette holding the tissue.

18. The sample sectioning device of claim 17, further comprising a control device that is operable to send control signals to the sample sectioning device, wherein the control device has a user input device to allow a user to invoke the logic to cause the sample sectioning device to autonomously remove the given thickness of the sample.

19. The sample sectioning device of claim 1, further comprising a wireless control device that is operable to send wireless control signals to the sample sectioning device.

20. A sample sectioning device comprising:
a cutting mechanism that is operable to cut sections from a sample;
a sample holder that is operable to hold the sample;
a drive system coupled with the sample holder, the drive system operable to drive movement between the sample held by the sample holder and the cutting mechanism;
a surface orientation sensor that is operable to sense an orientation of a surface of the sample held by the sample holder; and
logic to cause the sample sectioning device to remove a given thickness of the sample concealing a tissue within the sample, the given thickness associated with a thickness of a bottom of a cassette holding the tissue.

21. A sample sectioning device comprising:
a cutting mechanism that is operable to cut sections from a sample;
a sample holder that is operable to hold the sample;
a drive system coupled with the sample holder, the drive system operable to drive movement between the sample held by the sample holder and the cutting mechanism;
a surface orientation sensor that is operable to sense an orientation of a surface of the sample held by the sample holder, and wherein the surface orientation sensor comprises a first member capable of rotating about a first axis and a second member capable of rotating about a second axis different than the first axis; and
a wireless control device that is operable to send wireless control signals to the sample sectioning device.

* * * * *